United States Patent
Holmes

(10) Patent No.: US 8,992,402 B2
(45) Date of Patent: Mar. 31, 2015

(54) SYSTEM FOR BLOOD SEPARATION WITH SIDE-TAPPED SEPARATION CHAMBER

(75) Inventor: Brian M. Holmes, Evergreen, CO (US)

(73) Assignee: Terumo BCT, Inc., Lakewood, CO (US)

(*) Notice: Subject to any disclaimer, the term of this patent is extended or adjusted under 35 U.S.C. 154(b) by 574 days.

(21) Appl. No.: 13/478,684

(22) Filed: May 23, 2012

(65) Prior Publication Data

US 2012/0316051 A1  Dec. 13, 2012

Related U.S. Application Data

(60) Provisional application No. 61/496,164, filed on Jun. 13, 2011.

(51) Int. Cl.
*B04B 5/04* (2006.01)
*A61M 1/36* (2006.01)

(52) U.S. Cl.
CPC ............ *A61M 1/3693* (2013.01); *B04B 5/0442* (2013.01); *B04B 2005/0471* (2013.01); *B04B 2005/045* (2013.01); *A61M 1/3696* (2014.02)
USPC .......................................................... 494/42

(58) Field of Classification Search
CPC ... A61M 1/3693; A61M 1/3696; A61M 1/38; B04B 4/0442; B04B 2005/0442; B04B 2005/045; B04B 2005/0471; B04B 2005/0492
See application file for complete search history.

(56) References Cited

U.S. PATENT DOCUMENTS

| | | |
|---|---|---|
| 4,187,979 A | 2/1980 | Cullis et al. |
| 4,939,087 A | 7/1990 | Van Wie et al. |
| 5,405,308 A | 4/1995 | Headley et al. |
| 5,674,173 A | 10/1997 | Hlavinka et al. |
| 5,722,926 A | 3/1998 | Hlavinka et al. |
| 5,792,372 A | 8/1998 | Brown et al. |
| 5,858,251 A | 1/1999 | Borchardt et al. |
| 5,906,570 A | 5/1999 | Langley et al. |
| 5,913,768 A | 6/1999 | Langley et al. |
| 5,939,319 A | 8/1999 | Hlavinka et al. |
| 5,951,877 A | 9/1999 | Langley et al. |
| 6,022,306 A | 2/2000 | Dumont et al. |
| 6,053,856 A | 4/2000 | Hlavinka |
| 6,071,422 A | 6/2000 | Hlavinka et al. |

(Continued)

FOREIGN PATENT DOCUMENTS

WO  98/18403 A1  5/1998

OTHER PUBLICATIONS

PCT/US2012/039119, "International Search Report and Written Opinion," mailed Sep. 11, 2012.

*Primary Examiner* — Timothy Cleveland
(74) *Attorney, Agent, or Firm* — John R. Merkling; Elizabeth J. Reagan; René A. Pereyra

(57) ABSTRACT

A disposable blood separation set and a centrifugal blood processing system comprising a blood processing chamber adapted to be mounted on a rotor of a centrifuge; a frustro-conical cell separation chamber in fluid communication with the processing chamber, the cell separation chamber having an inlet, and outlet and a side tap outlet adjacent the inlet. The inlet may protrude into the cell separation chamber forming a circumferential well surrounding the protruding inlet. The side tap outlet may connect to the well. The set and system comprise means for selectively drawing fluid from either the outlet or the side tap outlet.

20 Claims, 4 Drawing Sheets

(56) References Cited

U.S. PATENT DOCUMENTS

| | | |
|---|---|---|
| 6,334,842 B1 | 1/2002 | Hlavinka et al. |
| 6,352,499 B1 | 3/2002 | Geigle |
| 6,354,986 B1 | 3/2002 | Hlavinka et al. |
| 6,514,189 B1 | 2/2003 | Hlavinka et al. |
| 6,574,173 B1 | 6/2003 | Manes |
| 7,029,430 B2 | 4/2006 | Hlavinka et al. |
| 7,201,848 B2 | 4/2007 | Antwiler et al. |
| 7,549,956 B2 | 6/2009 | Hlavinka et al. |
| 7,588,692 B2 | 9/2009 | Antwiler et al. |
| 7,857,744 B2 | 12/2010 | Langley et al. |
| 7,963,901 B2 | 6/2011 | Langley et al. |
| 8,066,888 B2 | 11/2011 | Sweat et al. |
| 8,226,537 B2 | 7/2012 | Pittinger et al. |
| 2006/0086675 A1* | 4/2006 | Purdum ............... 210/787 |
| 2006/0147895 A1 | 7/2006 | Purdum |
| 2007/0102374 A1 | 5/2007 | Kolenbrander |
| 2010/0065483 A1* | 3/2010 | Langley et al. ............ 210/195.3 |

* cited by examiner

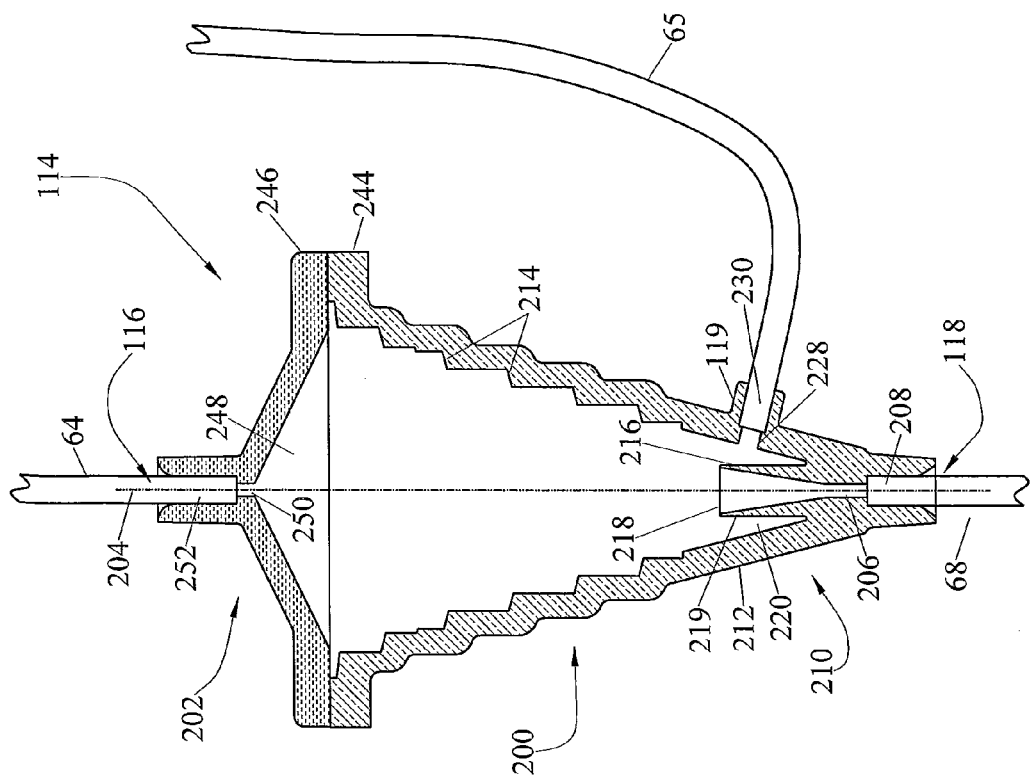
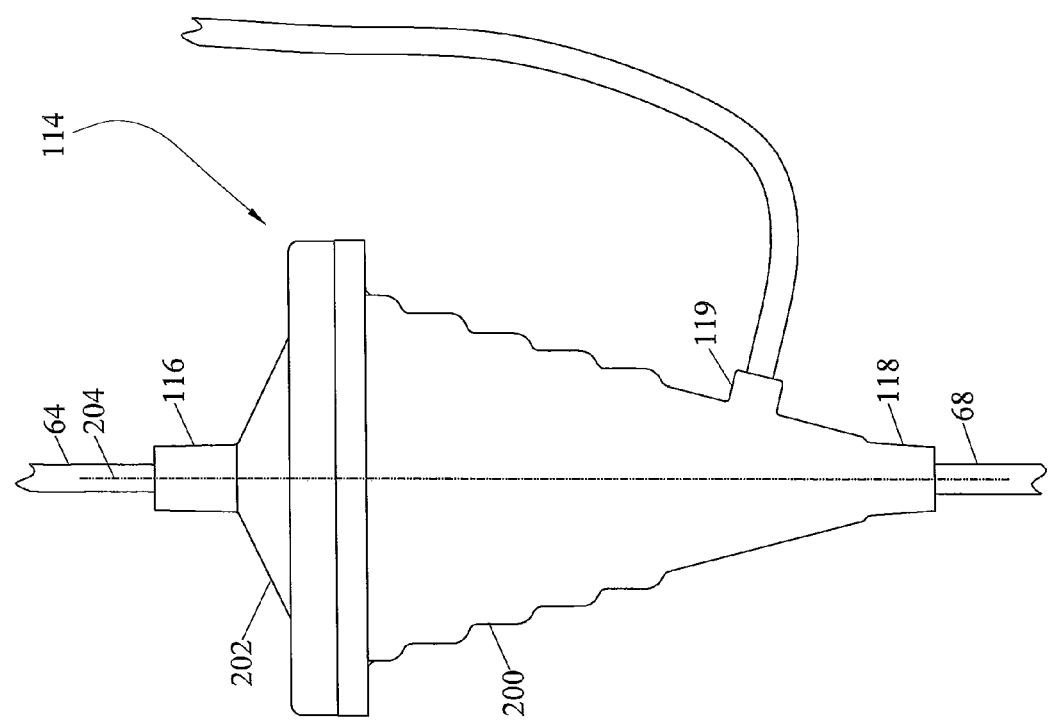
FIG. 5
FIG. 4

SYSTEM FOR BLOOD SEPARATION WITH SIDE-TAPPED SEPARATION CHAMBER

CROSS-REFERENCE TO RELATED APPLICATION

This application claims the priority of U.S. Provisional Application Ser. No. 61/496,164, filed on Jun. 13, 2011. The disclosure of the above-identified application is hereby incorporated by reference in its entirety as if set forth herein in full for all that it teaches and for all purposes.

BACKGROUND OF INVENTION

Blood collection and processing play important roles in the worldwide health care system. In conventional large scale blood collection, blood is removed from a donor or patient, separated into its various blood components via centrifugation, filtration, or elutriation and stored in sterile containers for future infusion into a patient for therapeutic use. The separated blood components typically include fractions comprising red blood cells, white blood cells, platelets, and plasma. Separation of blood into its components can be performed continuously during collection or can be performed subsequent to collection in batches, particularly with respect to the processing of whole blood samples. Separation of blood into its various components under highly sterile conditions is critical to many therapeutic applications.

Recently, apheresis blood collection techniques have been adopted in many large scale blood collection centers wherein a selected component of blood is collected and the balance of the blood is returned to the donor during collection. In apheresis, blood is removed from a donor and immediately separated into its components by on-line blood processing methods. Typically, on-line blood processing is provided by density centrifugation, filtration, or diffusion-based separation techniques. One or more of the separated blood components are collected and stored in sterile containers, while the remaining blood components are directly re-circulated to the donor. An advantage of this method is that it allows more frequent donation from an individual donor because only a selected blood component is collected and purified. For example, a donor undergoing plateletpheresis, whereby platelets are collected and the non-platelet blood components are returned to the donor, may donate blood as often as once every fourteen days.

Apheresis blood processing also plays an important role in a large number of therapeutic procedures. In these methods, blood is withdrawn from a patient undergoing therapy, separated, and a selected fraction is collected while the remainder is returned to the patient. For example, a patient may undergo leukapheresis prior to radiation therapy, whereby the white blood cell component of his blood is separated, collected and stored to avoid exposure to radiation.

Both conventional blood collection and apheresis systems typically employ differential centrifugation methods for separating blood into its various blood components. In differential centrifugation, blood is circulated through a sterile blood processing vessel which is rotated at high rotational speeds about a central rotation axis. Rotation of the blood processing vessel creates a centrifugal force directed along rotating axes of separation oriented perpendicular to the central rotation axis of the centrifuge. The centrifugal force generated upon rotation separates particles suspended in the blood sample into discrete fractions having different densities. Specifically, a blood sample separates into discrete phases corresponding to a higher density fraction comprising red blood cells and a lower density fraction comprising plasma. In addition, an intermediate density fraction comprising platelets and leukocytes forms an interface layer between the red blood cells and the plasma. Descriptions of blood centrifugation devices are provided in U.S. Pat. No. 5,653,887 and U.S. Pat. No. 7,033,512.

To achieve continuous, high throughput blood separation, extraction or collect ports are provided in most blood processing vessels. Extraction ports are capable of withdrawing material from the separation chamber at adjustable flow rates and, typically, are disposed at selected positions along the separation axis corresponding to discrete blood components. To ensure the extracted fluid exiting a selected extraction port is substantially limited to a single phase, however, the phase boundaries between the separated blood components must be positioned along the separation axis such that an extraction port contacts a single phase. For example, if the fraction containing white blood cells resides too close to the extraction port corresponding to platelet enriched plasma, white blood cells may enter the platelet enriched plasma stream exiting the blood processing vessel, thereby degrading the extent of separation achieved during blood processing. Although conventional blood processing via density centrifugation is capable of efficient separation of individual blood components, the purities of individual components obtained using this method is often not optimal for use in many therapeutic applications.

As a result of the inability to achieve optimal purity levels using centrifugation separation alone, a number of complementary separation techniques based on filtration, elutriation in a cell separation chamber and affinity-based techniques have been developed to achieve the optimal purities needed for use of blood components as therapeutic agents. These techniques, however, often reduce the overall yield realized and may reduce the therapeutic efficacy of the blood components collected. Exemplary methods and devices of blood processing via filtration, elutriation and affinity based methods are described in U.S. Pat. No. 6,334,842.

A centrifugal blood component separation apparatus has been described in commonly assigned U.S. Pat. No. 7,605,388, for instance. As described in U.S. Pat. No. 7,605,388, an optical cell may be configured such that white blood cells can be extracted through a first extraction port, plasma and/or platelets can be extracted through second extraction port, and red blood cells can be extracted through third extraction port. As also mentioned in U.S. Pat. No. 7,605,388 (but not shown), optical cells of a blood separation vessel can include one or more dams positioned proximate to the extraction ports to facilitate selective extraction of separated blood components having reduced impurities arising from adjacent components. The use of dams in blood processing via density centrifugation is known in the art and described in U.S. Pat. Nos. 6,053,856; 6,334,842 and 6,514,189.

SUMMARY OF THE INVENTION

This invention provides methods, devices and device components for improving the processing of fluids comprising fluid components, such as blood, components of blood and fluids derived from blood. Methods, devices and device components of the present invention are capable of monitoring and controlling separation of blood into discrete components and subsequent collection of selected components. In particular, it has been found that white blood cells may be extracted from the bottom of a fluidized bed leuko-reduction chamber (or cell separation chamber) while plasma and platelets are removed from the top of the separation chamber. The system and method may enable collection of white blood cells with fewer platelets.

A function of the centrifuge blood processing system described herein may be the collection of white blood cells or other selected blood components such as mesenchymal stem cells. In a preferred embodiment, certain functions of the centrifugal blood separator are controlled by an optical monitoring system. A cell separation chamber, adapted to be mounted on a rotor of the centrifuge blood processing system, comprises an inlet for receiving plasma, platelets and white blood cells, or "buffy coat", an outlet for ejecting plasma and platelets from the separation chamber, and a side tap outlet for ejecting white blood cells and plasma from the separation chamber. Red blood cells or plasma may be collected or returned to a donor. White cells or other components such as mesenchymal stem cells and plasma may be collected for therapeutic purposes.

According to an embodiment, an optical cell of a circumferential blood processing vessel comprises at least a buffy coat extraction port and a red blood cell extraction port. White cells collect at the buffy coat extraction port. This configuration allows white cell-containing buffy coat to be withdrawn from the blood processing vessel through the buffy coat extraction port for further separation in the fluidized-bed filtration chamber or cell separation chamber. The cell separation chamber has a generally conical shape, with a buffy coat inlet at the apex of the cone and adapted to be mounted with the buffy coat inlet radially outwardly on the centrifuge rotor. A plasma outlet is centrally located in the base of the cone and is adapted to be mounted radially inwardly on the centrifuge rotor. The base may also have a slight conical shape to conduct platelets and plasma to the plasma outlet. The inlet comprises a pipe or tube extending into the interior of the separation chamber such that a circumferential well is formed between the pipe and an interior conical wall of the separation chamber. A side tap white blood cell extraction port penetrates the conical wall into the circumferential well. White blood cells ("WBC") fall into the well and white blood cells and plasma are withdrawn from the separation chamber through the side tap extraction port for collection.

A function of the apparatus and method described herein may be to reduce the loss of white blood cell product or selected cell components such as mesenchymal stem cells that can occur during periodic flushing of white blood cells through the platelet outlet, as in conventional separation chamber.

Further the apparatus may provide more continuous steady flow through a cell separation chamber, thereby providing a greater volume of blood components processed per unit time. Another feature may be to produce a collected white blood cell (or other selected cell types) product having fewer platelets than conventional collection methods, and thus improved purity.

According to an embodiment, collection flow rates out of the separation chamber may be reduced and the volume of WBC-containing fluid extracted from the separation chamber may be reduced. A low WBC extraction volume may be achieved with a cycled extraction rate through the side-tap port that may be triggered by detection of a saturated separation chamber by the optical sensor. Total flow through the separation chamber may be kept constant.

An embodiment may have a cell separation chamber for cell collection that is not limited by insufficient available plasma for flushing the selected cells through the platelet outlet, as in conventional separation chamber.

For donors whose blood has a high hematocrit, it has sometimes been difficult or impossible to reduce the RPM of the centrifuge rotor (and thereby reduce the gravitational field of the centrifuge) sufficiently to allow complete flushing of WBC out of the platelet outlet of a conventional separation chamber. An embodiment may not require a reduction in the centrifuge gravitational field when white blood cells are removed from the separation chamber.

These and other features and advantages of the invention will be apparent from the following description, drawings and claims.

BRIEF DESCRIPTION OF THE DRAWINGS

FIG. 4 is a plan view of the cell separation chamber of FIG. 3.

FIG. 5 is a cross-sectional view of the cell separation chamber of FIG. 4.

DETAILED DESCRIPTION

Figure 1:
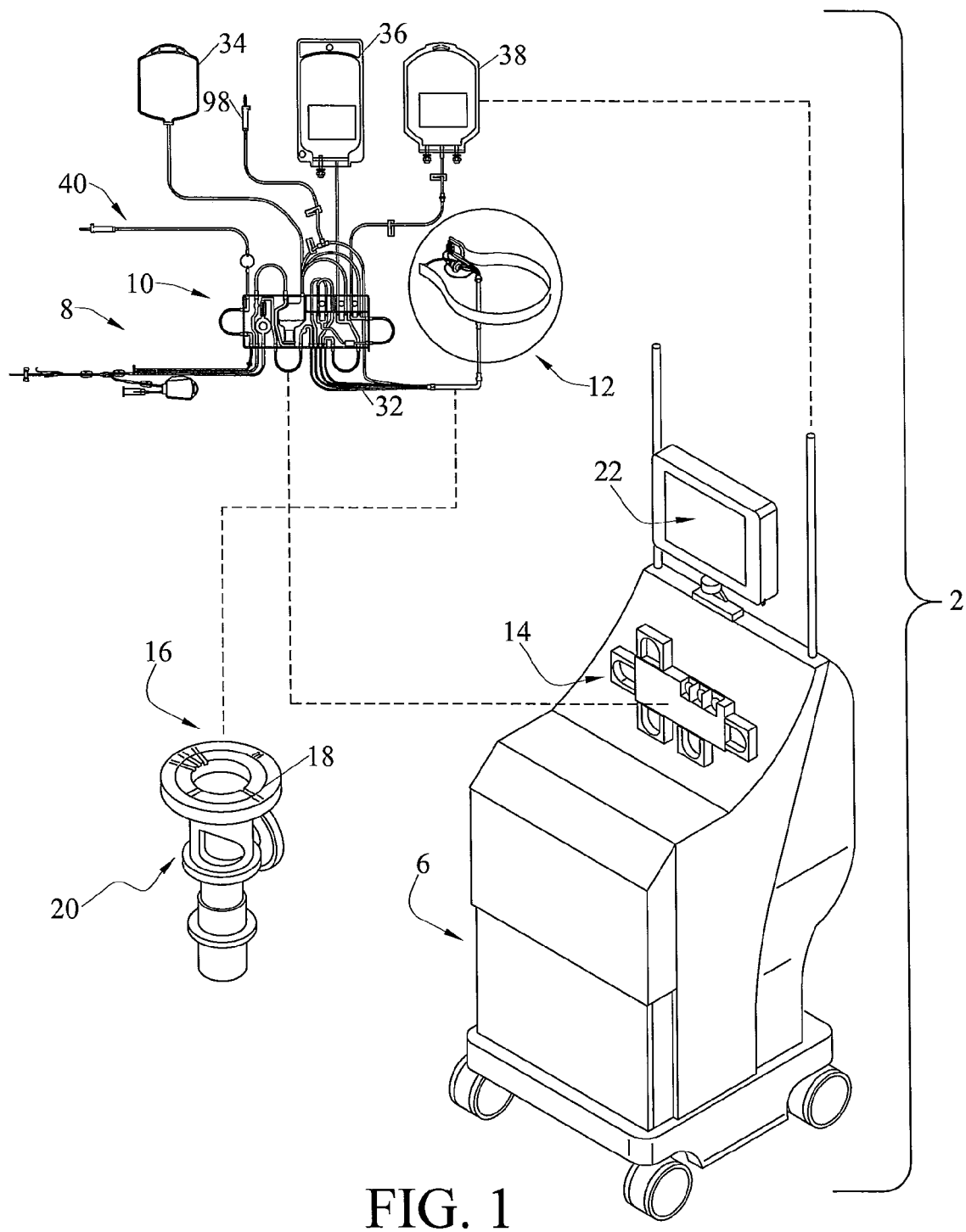
FIG. 1 is a schematic view of one embodiment of an apheresis system, which can be used in or with the present invention.

To describe the present invention, reference will now be made to the accompanying drawings. The present invention may be used with a blood processing apparatus such as a SPECTRA OPTIA® blood component centrifuge manufactured by CaridianBCT, Inc, or a TRIMA® or TRIMA ACCEL® blood component centrifuge also manufactured by CaridianBCT, Inc. The invention may also be used with other blood component centrifuges. The above-named centrifuges incorporate a one-omega/two-omega seal-less tubing connection as disclosed in U.S. Pat. No. 4,425,112 to provide a continuous flow of blood to and from the rotor of an operating centrifuge without requiring a rotating seal.

The an embodiment of the invention may comprise an improved leuko-reduction or cell separation chamber for removal of white blood cells ("WBC") or other selected types of cells such as mesenchymal stem cells from blood components. A related separation chamber is described in commonly-assigned U.S. application Ser. No. 12/209,793.

It is desirable for a separation chamber to separate greater than 99.99% of entrained WBC from platelet or plasma products obtained by centrifugal apheresis, which is an extremely high value. The process for this separation is based on the phenomenon of particle sedimentation in a fluid. The separated WBC consist of about 95% mononuclear cells (which are about 90% leukocytes and 10% monocytes) and about 5% granulocytes. To accommodate the apheresis collection process, the separation chamber may function in an automatic mode as a continuous-feed process. This requires an overflowing saturated bed of platelets above a bed of mononuclear cells, which continuously accumulate during the collection. The saturated bed requirement operates in the dense-phase flow regime, which is characterized by high cell density. After a quantity or bolus of white blood cells are collected in the separation chamber, the WBC are removed from the chamber for collection. In devices with conventional separation chambers, this may be accomplished by reducing the rotational speed of the centrifuge and increasing the flow rate of plasma through the separation chamber, thus pushing the WBC bolus out of the outlet port. An additional line or tube, however, is connected to a side wall of the separation chamber through a side tap, near an inlet to the chamber. The WBC are drawn out of the separation chamber through the side tap, which is "down hill" with respect to the gravitational field created by the centrifuge apparatus. There is little or no need to change the speed of the centrifuge, nor is an increased inlet flow of plasma needed to flush the collected WBC through the outlet. However, briefly pausing a pump in the collect line will pack WBC in the separation chamber, allowing the cells to ultimately be removed from the separation chamber in a smaller volume. A relatively small amount of additional plasma may be allowed to flow back into the chamber from the outlet, or to flow in from the inlet to displace the WBC and fluid being withdrawn through the side tap. Preferably, the separation chamber is oriented such that the side tap is on the trailing side of the separation chamber when the chamber is mounted on the rotor. That is, as the rotor turns, the side tap is on the side of the separation chamber that passes an observer last. A protruding inlet port may also be provided coupled to the inlet of the separation chamber and adjacent the side tap outlet.

The protruding inlet port is a tube that transfers the entering flow past a critical area where the wall of the chamber forms the apex of a cone opening into the body of the chamber and past a side tap outlet for withdrawing WBC from the chamber. The protruding port may eliminate a flow path along the wall that is caused by Coriolis acceleration. Coriolis acceleration pushes fluid entering the chamber towards the leading chamber wall. This entering fluid contains high concentrations of WBC. If the fluid is pushed against the wall, rather than remaining generally in the center of the chamber, the fluid tends to flow up the wall, circumventing the bed of white blood cells and platelets that captures WBC in the chamber by sedimentation forces. In addition, the protruding inlet port blocks direct entry into the side tap outlet, thus compelling the WBC to enter the area of the fluidized bed within the separation chamber.

A preferred blood apheresis system 2 for use with the present invention is schematically illustrated in FIG. 1. System 2 provides for a continuous blood component separation process. Generally, whole blood is withdrawn from a donor and is substantially continuously provided to a blood component separation device 6 where the blood is separated into various components and at least one of these blood components is collected from the device 6. One or more of the separated blood components may be either collected for subsequent use or returned to the donor.

In the blood apheresis system 2, blood is withdrawn from the donor and directed through a bag and tubing set 8, which includes an extracorporeal tubing circuit 10, and a blood processing vessel 12, which together define a closed, sterile and disposable system. The set 8 is adapted to be mounted in the blood component separation device 6. The separation device 6 includes a pump/valve/sensor assembly 14, which interfaces with the extracorporeal tubing circuit 10, and a centrifuge assembly 16, which interfaces with the blood processing vessel 12.

The centrifuge assembly 16 may include a channel 18 in a rotatable rotor assembly 20, which provides the centrifugal forces required to separate blood into its various blood component types by centrifugation. The blood processing vessel 12 may then be fitted within the channel 18. Blood can flow substantially continuously from the donor, through the extracorporeal tubing circuit 10, and into the rotating blood processing vessel 12. Within the blood processing vessel 12, blood may be separated into various blood component types and at least one of these blood component types (e.g., white blood cells, platelets, plasma, or red blood cells) may be removed from the blood processing vessel 12. Blood components that are not being retained for collection or for therapeutic treatment (e.g., platelets and/or plasma) are also removed from the blood processing vessel 12 and returned to the donor via the extracorporeal tubing circuit 10. Various alternative apheresis systems (not shown) may also make use of the present invention, including batch processing systems (non-continuous inflow of whole blood and/or non-continuous outflow of separated blood components) or smaller scale batch or continuous RBC/plasma separation systems, whether or not blood components may be returned to the donor.

Operation of the blood component separation device 6 is controlled by one or more processors included therein, and may advantageously comprise a plurality of embedded computer processors to accommodate interface with PC user facilities (e.g., CD ROM, modem, audio, networking and other capabilities). In order to assist the operator of the apheresis system 2 with various aspects of its operation, the blood component separation device 6 includes a graphical interface 22 with an interactive touch screen.

Figure 2:
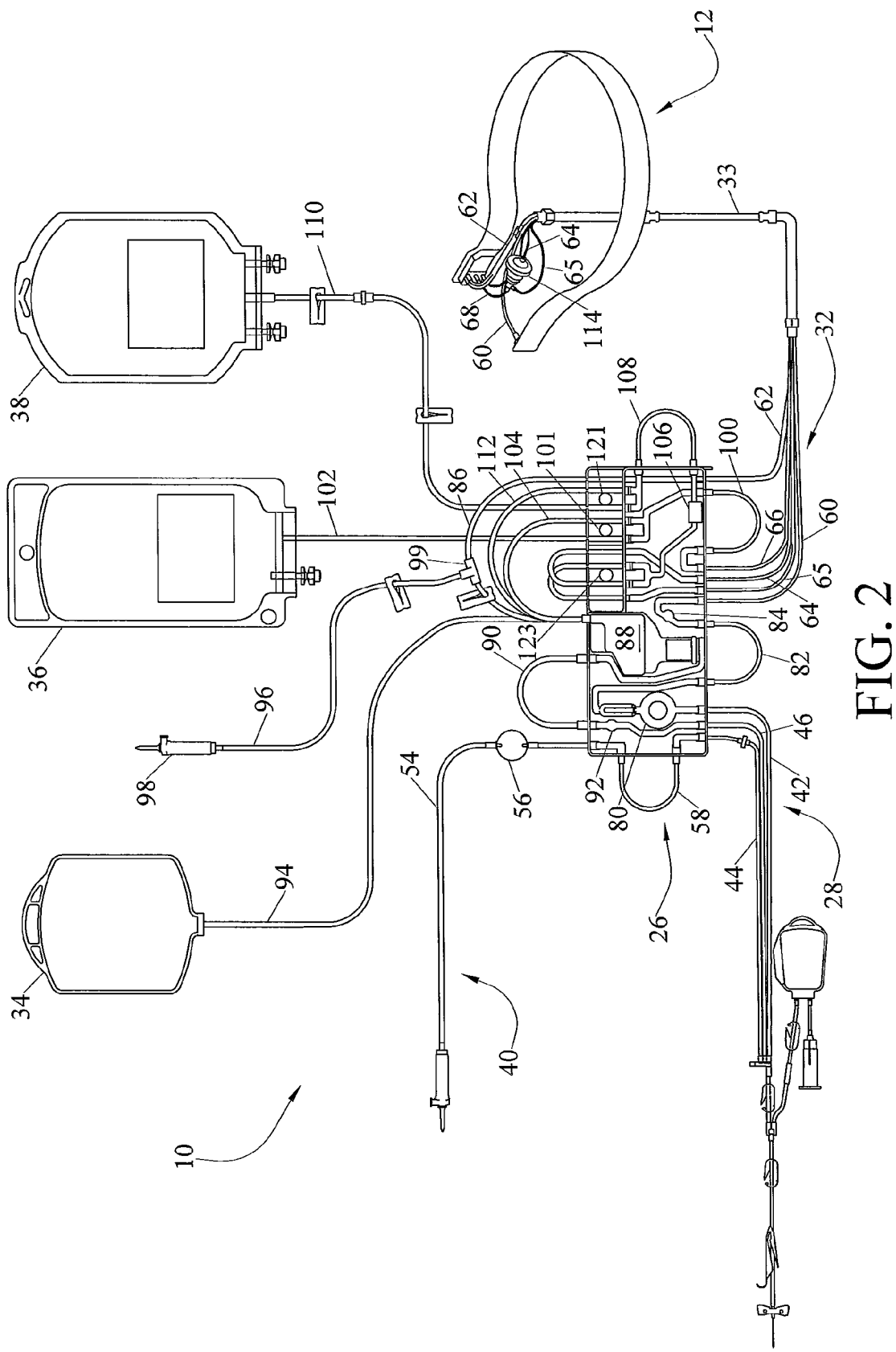
FIG. 2 illustrates a tubing and bag set including an extracorporeal tubing circuit, a cassette assembly, collection bag assembly, a blood processing vessel, and a cell separation chamber for use in or with the system of FIG. 1.

An extracorporeal tubing circuit 10, shown in FIG. 2, may include a cassette 26 and a number of tubing/collection assemblies 28, 32, 34, 36, 38 and 40. A blood removal-return tubing assembly 28 provides a needle interface for withdrawing blood from a donor to the remainder of the tubing circuit 10 and for returning blood components and other fluids to the donor. A single needle configuration is shown, but a double needle interface may also be used. Three lines 42, 44, 46 are provided in blood removal-return tubing assembly 28 for removal of blood from the donor. A cassette 26 is connected between the tubing assembly 28, which connects to the donor, and blood inlet/blood component tubing line sub-assembly 32, which provides the interface between cassette 26 and blood processing vessel 12. The cassette 26 orients tubing segments in predetermined spaced relationships within the cassette 26 for ultimate engagement with valve members on apheresis device 6. Such valves will, when activated, control flow through loops and tubing.

The tubing line sub-assembly 32 comprises five lines 60, 62, 64, 65, and 66, shown in FIG. 2, for transport of blood and components to and from the processing vessel 12. The five lines are encased in a sheath 33 that allows the one omega-two omega motion described in U.S. Pat. No. 4,425,112. An anticoagulant tubing assembly 40, a vent bag 34, a plasma collection assembly 36, and a white blood cell collection bag 38 are also interconnected with cassette 26. Optionally, a red blood cell collection assembly might also be provided through an auxiliary line 96, as is known in the art. The extracorporeal tubing circuit 10 and blood processing vessel 12 are pre-connected to form a closed, sterilized, disposable assembly for a single use.

When the tubing circuit 10 has been mounted on the blood component separation device 6, saline solution (not shown) primes the tubing circuit through a line 54 and filter 56 (see FIG. 2). Saline flows through an internal passageway in the cassette 26 and through the line 44 to the distal end of the blood removal-return assembly 28. Saline can then flow up a blood withdrawal line 42 into the other tubes and passageways of the circuit 10 in preparation for blood processing. A supply or bag (not shown) of anticoagulant can then be connected to a distal end of the anticoagulant tubing assembly 40 in place of a saline supply. Anticoagulant solution flows past the filter 56 and a first pump loop 58 through the anticoagulant line 44 to the distal end of the blood removal assembly. The pump loop 58 and other pump loops described herein couple with peristaltic pumps on the blood processing device 6 in a known manner. The device 6 controls the direction and rate of flow of the fluids described herein by controlling the speed and direction of the peristaltic pumps and the position of various valves.

The blood removal line 42 conducts blood into the cassette 26, where the blood passes a first pressure sensor 80 and a second pump loop 82. A second pressure sensor 84, between second pump loop 82 with its associated pump and blood inflow line 60 to the blood processing vessel 12, senses the fluid pressure effective at an inlet to the blood processing vessel 12. Emanating from blood processing vessel 12 is an RBC outlet tubing line 62 of the blood inlet/blood component tubing assembly 32. The outlet tubing line 62 connects to an external loop 86 to a return reservoir 88. The return reservoir 88 contacts sensors on the device 6 that detect low and high fluid levels. The device 6 keeps the fluid in the reservoir between these two levels by controlling flow out of the reservoir past a return pump loop 90 and a return pressure sensor 92. As the fluid level in the reservoir 88 is constantly rising and falling, a vent bag 34 connects to the reservoir 88 through a vent tube 94. Air can flow between the reservoir 88 and the vent bag 34 in a sterile manner. Fluid flows into a return tube 46 in the blood removal-return assembly 28. The blood removal-return assembly 28 also comprises the line 44 for priming or anti-coagulant as described above. If desired, red blood cells could be withdrawn through auxiliary line 96 and collected in a collection bag (not shown). Alternatively, a bag containing replacement fluid (not shown) is connect to a spike or Luer connector 98 on the replacement line, allowing replacement fluid to pass through the return loop 86 into the reservoir 88. Blood components and replacement fluid are then returned to the donor. In the present embodiment, replacement line 96 is connected to return loop 86 through a junction 99 and manual closures or clamps are provided to direct the flow of red blood cells and replacement fluid. Equivalently, it is known to couple the red blood cell line 62 to a peristaltic pump and to provide an automatic valve to select blood flow paths, as shown, for instance in U.S. patent application Ser. No. 12/959,987.

Plasma may also be collected from the blood processing vessel 12 into plasma bag 36. When desired, plasma is withdrawn from the blood processing vessel 12 through plasma line 66 to a pump loop 100. A valve 101 diverts the plasma either into a collect tube 102 to the plasma bag 36, or into connecting loop or line 104 to the reservoir 88. Excess plasma in the reservoir 88 is returned to the donor in the same way as red blood cells, as described above.

White blood cells and platelets flow out of the blood processing vessel 12 through a cell line 68 into a cell separation chamber 114, which is further described below. The contents of the separation chamber flow out of the separation chamber either through a primary outlet line 64 at the primary outlet 116 (see FIG. 4) or through a secondary outlet line 65 at a secondary or side tap outlet 119 near the inlet 118 of the separation chamber, as will be discussed below. The primary and secondary outlet lines 64, 65 pass through the tubing line sub-assembly 32 and sheath 33 to the cassette 26. A valve 123 selects between the two outlet lines 64, 65, closing one line and opening the other, thereby allowing fluid to be withdrawn from two different locations in the separation chamber 114. In the cassette 26, the fluid from the selected outlet line passes a red-green photo sensor 106, which may be used to control periodic flushing of white blood cells out of the cell separation chamber 114 into the collect bag 38. The selected cells flow through a pump loop or common line 108, which engages a peristaltic pump on the separation device 6. The pump loop 108 connects to a valved passageway in the cassette 26. The blood processing device 6 can control a valve 121 to direct white blood cells or other selected cells either into a collect tube 110 and thence into the collect bag 38, or into a connection loop or line 112 and thence into the reservoir 88. For platelet collection, excess white blood cells in the reservoir 88 may be returned to the donor in the same way as red blood cells and plasma, as described above. Alternatively, for mesenchymal stem cell (MNC) collection, wherein platelets are usually returned to the donor, the MNC are withdrawn through the side tap outlet 119 into the collect tube 110 for storage in the collect bag 38.

The process of extracting cells from the separation chamber has been described using a single pump 128 (see FIG. 3) connected to loop 108 for both line 64 from the to primary outlet 116 and for the secondary outlet line 65 from the side tap outlet 119. Clearly, an additional loop and pump could also be provided such that each of the outlet lines 64, 65 would be provided with a dedicated loop and pump. The valve 123 would not be required to selectively couple the two lines 64, 65 to a shared loop and pump. Such variations are within the scope of one skilled in the art, without departing from the teachings of the present invention.

During a blood removal, whole blood will be passed from a donor into tubing line 42 of blood removal tubing assembly 28. The blood is pumped by the device 6 via pump loop 82, to the blood processing vessel 12 via the cassette 26 and line 60 of the blood inlet/blood component tubing assembly 32. Separation processing then occurs on a substantially continuous basis in the blood processing vessel 12, i.e., blood flows substantially continuously therein, is continuously separated and flows as separated components therefrom. After separation processing in vessel 12, uncollected blood components are transferred from the processing vessel 12 to and through cassette 26 and into reservoir 88 of cassette 26, which is filled up to a predetermined level. The blood component separation device 6 may initiate a blood return submode wherein components may be returned to the donor through return line 46. The cycle between blood removal and blood return submodes will continue until a predetermined amount of blood components have been harvested. In an alternative double needle scheme, as is known in the art, blood may be removed from the donor and returned to a donor through two separate needles. See, for example, US Patent application 2010/160137.

A bracket (not shown) is provided on a top surface of the centrifuge assembly 16. The bracket releasably holds the cell separation chamber 114 on the centrifuge assembly 16 so that an outlet 116 of the cell separation chamber 114 is positioned closer to the axis of rotation than an inlet 118 of the chamber 114. The bracket orients the chamber 114 on the centrifuge assembly 16 with a longitudinal axis of the cell separation chamber 114 in a plane transverse to the rotor's axis of rotation. In addition, the bracket is arranged to hold the cell separation chamber 114 on the centrifuge assembly 16 with the cell separation chamber outlet 116 facing the axis of rotation. Although the chamber 114 is preferably on a top surface of the centrifuge assembly 16, the chamber 114 could also be secured to the centrifuge assembly 16 at alternate locations, such as beneath the top surface of the centrifuge assembly 16.

Figure 3:
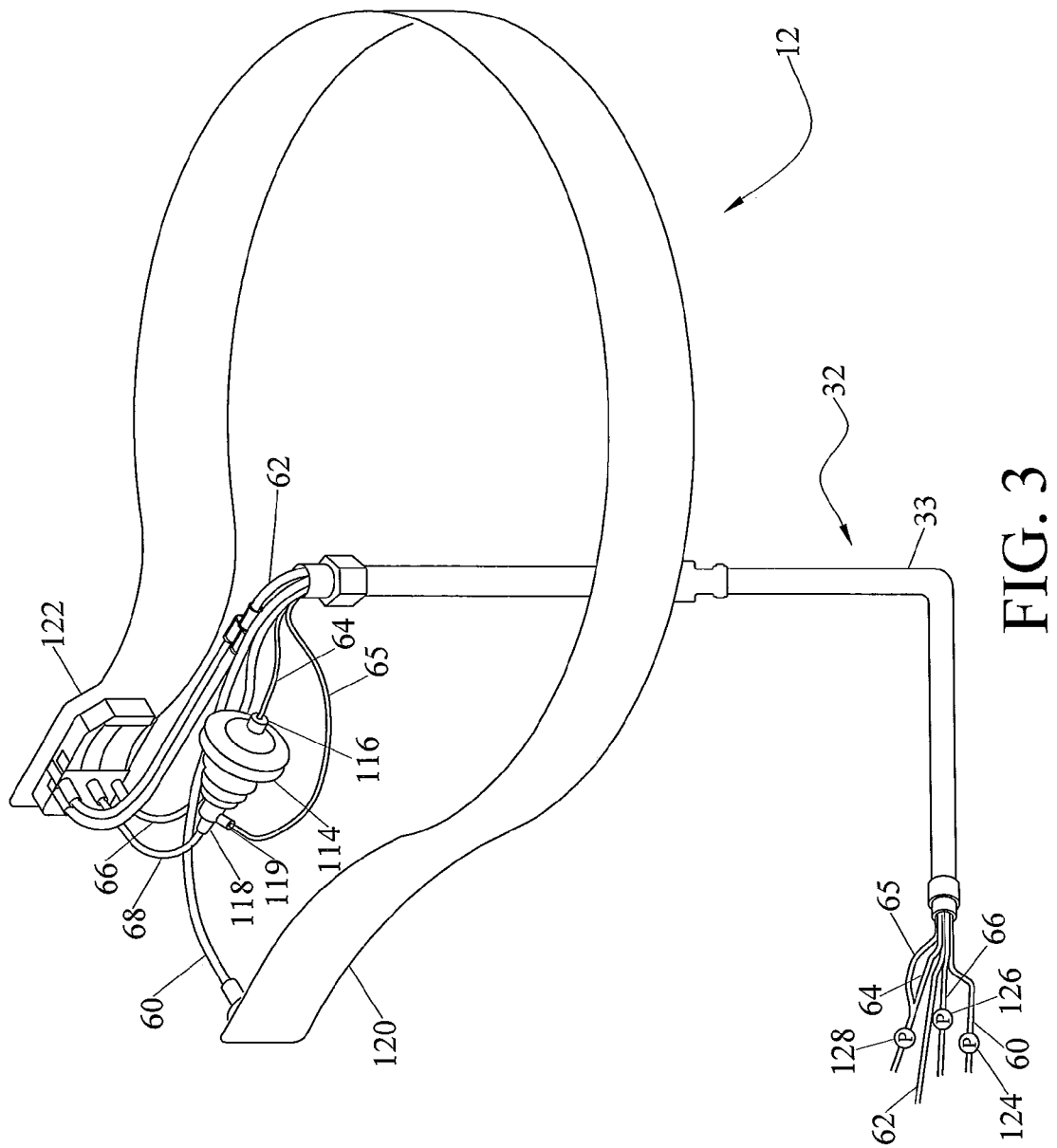
FIG. 3 is a perspective view of a blood processing vessel and the cell separation chamber.

FIG. 3 schematically illustrates the blood processing vessel 12 and cell separation chamber 114. The blood processing vessel 12 has a generally annular flow path and includes an inlet portion 120 and an outlet portion 122. The inflow tube 60 connects to the inlet portion 120 for conveying a fluid to be separated, such as whole blood, into the blood processing vessel 12. During a separation procedure, substances entering the inlet portion 120 flow around the vessel 12 and stratify according to differences in density in response to rotation of the centrifuge assembly 16. The outlet portion 122 includes outlets for the RBC line 62, the plasma line 66, and buffy coat or white blood cell line 68 for removing separated substances from the blood processing vessel 12. Each of the components separated in the vessel 12 is collected and removed in only one area of the vessel 12, namely the outlet portion 122.

The outlet of the line 68 is connected to the cell separation chamber inlet 118 to pass intermediate density components, including white blood cells or mesenchymal stem cells (MNC), into the cell separation chamber 114. Components initially separated in the blood processing vessel 12 are further separated in the cell separation chamber 114. For example, white blood cells could be separated from plasma and platelets in the cell separation chamber 114. This further separation takes place by forming a saturated fluidized bed of particles in the cell separation chamber 114. Plasma and platelets would flow out of the cell separation chamber 114 while white blood cells were retained in the chamber. Similarly, granulocytes could be separated from red blood cells in like manner.

As schematically shown in FIG. 3, a plurality of pumps 124, 126, and 128 are provided for adding and removing substances to and from the blood processing vessel 12 and cell separation chamber 114. An inflow pump 124 is coupled to the inflow line 60 at pump loop 82 (FIG. 2) to supply the substance to be separated, such as whole blood, to the inlet portion 120. In addition, a first collection pump 126 is coupled at loop 100 to the plasma line 66. A second collection pump 128 is coupled to the collection line 64 and the cell collection line 65 at loop 108. The second collection pump 128 draws liquid and particles either from the cell separation chamber outlet 116 or from the side tap outlet 119 and causes liquid and particles to enter the cell separation chamber 114 via the cell separation chamber inlet 118. In the present embodiment, plasma and platelets are usually withdrawn from the outlet 116 of the cell separation chamber 114 through line 64. In the prior art, collected white blood cells or MNC or other components would be flushed from the chamber 114 through the first cell collection line 64 by either increasing the fluid flow through the chamber 114 or by slowing the rotor or both. On the other hand, in the illustrated embodiment, the second cell collection line 65 connects to the cell collection chamber 114 near the inlet 118 at the side tap connection 119. A valve 123 on the blood component separation device 6 selectively closes the collection lines 64, 65. The first and second collection lines 64, 65 are joined into a common tube past the valve 123 and form loop 108. Thus, the peristaltic pump 128, which is coupled to loop 108, can draw fluid either from the outlet 116 or the side tap outlet 119, depending on the valve 123. Alternatively, as described above, a dedicated pump and loop could be provided for each of the collect lines 64, 64 without departing from the teachings of the present invention.

During the formation of the fluidized bed of cells in the chamber 114, platelet rich plasma (PRP) or platelets would ordinarily be drawn from the outlet 116 through tube 64. During expression of collected cells (e.g., MNC), the collected cells would be drawn through the side tap 119 and second collection line 65. Since the collected cells would be relatively heavier than plasma, they would tend to fall towards the side tap 119 and could more easily be withdrawn from the chamber 114. Beyond pump 128, loop 108 again divides into two lines 110, 112. A valve 121 on the device 6 selectively opens and closes the lines. Line 112 is coupled to the reservoir 88 and ordinarily returns PRP to the donor. Line 110 is coupled to a collect bag 38 and allows the collected cells to flow into the collect bag 38.

The first collection pump 126, which is coupled to loop 100, removes primarily low-density substances such as plasma directly from the blood processing vessel 12 via the plasma line 66. The plasma could either be collected in plasma bag 36 through line 102, or returned to the donor through connecting loop or line 104 and the reservoir 88. Valve 101 selectively opens and closes the lines 102, 104 to direct the flow of plasma either to the bag 36 or to the reservoir 88.

The pumps 124, 126, and 128 are peristaltic pumps, which prevent significant damage to blood components. The pumps 124, 126, and 128 control the flow rate of substances flowing to and from the blood processing vessel 12 and the cell separation chamber 114. A saturated fluidized bed of particles is maintained within the cell separation chamber 114 to cause other particles to be retained in the cell separation chamber 114.

Blood within the processing vessel 12 is subjected to centrifugal force causing components of the blood components to separate. The components of whole blood stratify in order of decreasing density as follows: (1) red blood cells, (2) white blood cells, (3) platelets, and (4) plasma. The controller regulates the rotational speed of the centrifuge channel assembly 16 to ensure that this particle stratification takes place. A layer of red blood cells (high density components) forms along the outer wall of the processing vessel 12 and a layer of plasma (lower density components) forms along the inner wall of the processing vessel 12. Between these two layers, the intermediate density platelets and white blood cells (intermediate density components) form a buffy coat layer. Preferably, the separation is observed in two dimensions by a camera and controlled as described in U.S. Pat. No. 7,422,693, which is incorporated herein by reference.

The cell separation chamber is shown in detail in FIG. 4 and FIG. 5. FIG. 5 is a cross section of FIG. 4 taken in the plane of the illustration. The cell separation chamber 114 may be constructed in two pieces, a main body 200 and a cap 202, both being symmetrical around an axis 204. The main body 200 has an inlet 118 comprising a through bore 206 and a concentric stopped bore 208. The diameter of the through bore 206 corresponds to the inside diameter of the cell line 68, while the diameter of the stopped bore 208 corresponds to the outside diameter of the line 68, so that the cell line 68 can be seated in the stopped bore 208 and a fluid passageway of constant diameter can be formed between the line 68 and the through bore 206. The through bore 206 opens into a frustro-conical segment 210. A wall 212 of the frustro-conical segment 210 may comprise a plurality of steps 214 which generally taper away from the axis 204. Straight or curved walls may also be used in the frustro-conical segment 210. The through bore 206 rises into the frustro-conical segment 210 through a protruding inlet 216. A mouth 218 of the protruding inlet 216 opens into the frustro-conical segment 210 spaced away from the wall 212, thereby forming a circumferential well 220 between the wall and the protruding inlet. A stream of fluid leaving the protruding inlet and entering the chamber is insulated from the effects of the wall 220 by a relatively static fluid layer. The stream is therefore less likely to adopt a flow path along the wall, under the influence of Coriolis forces, but rather will remain in the center of the chamber, allowing more uniform mixing of cells and other particles within the chamber. An inner surface 219 of the protruding inlet flares slightly outwardly towards the mouth 218 of the protruding inlet 216. This reduces the flow velocity of fluid passing through the protruding inlet and lessens Coriolis effects as the fluid enters the chamber.

In the illustrated embodiment, the main body 200 of the cell separation chamber 114 further comprises a circumferential flange 244, which is supported in the holder. The cap 202 comprises a rim 246 that fits against the flange 244. An interlocking groove and ridge (not shown) may be provided between the rim 246 and flange 244 for sealing, if desired. The cap 202 and main body 200 may be joined by ultrasonic welding or other suitable techniques as known in the art. The cap opens into an abrupt frustro-conical segment 248. The abrupt segment 248 tapers towards the axis 204. The abrupt segment 248 funnels blood components into the outlet 116 without excessive turbulence or damage to the blood components. The outlet 116 comprises a through bore 250 and a concentric stopped bore 252. The diameter of the through bore 250 corresponds to the inside diameter of the cell line 64, while the diameter of the stopped bore 252 corresponds to the outside diameter of the cell line 64, so that the line 64 can be seated in the stopped bore 252 and a fluid passageway of constant diameter can be formed between the line 64 and the through bore 250. The through bore 250 opens into the frustro-conical segment 248.

As described above, the separation chamber 114 further comprises a side tap outlet 119. The outlet 119 also comprises a through bore 228 and a concentric stopped bore 230. The diameter of the through bore 228 corresponds to the inside diameter of the cell line 65, while the diameter of the stopped bore 230 corresponds to the outside diameter of the cell line 65, so that the line 65 can be seated in the stopped bore 230 and a fluid passageway of constant diameter can be formed between the line 65 and the through bore 228.

The separation chamber 114 functions in an automatic mode as a continuous-feed process. An overflowing saturated bed of platelets forms above a bed of mononuclear cells, which continuously accumulate during the collection. The saturated bed requirement operates in the dense-phase flow regime, which is characterized by high cell density. After a quantity or bolus of white blood cells or other selected cells is collected in the separation chamber, the cells are removed from the chamber for collection. The selected cells may be drawn out of the separation chamber 114 through the side tap outlet 119, which is "down hill" with respect to the gravitational field created by the centrifuge apparatus. There is little or no need to change the speed of the centrifuge, nor is an increased inlet flow of plasma needed to flush the collected cells through the outlet 116. With the line 64 closed and the line 65 open, the collected cells are drawn out of the separation chamber for collection through the side tap outlet 119. A relatively small amount of additional plasma may be allowed to flow back into the chamber 114 from the outlet 116, or to flow in from the inlet 118 to displace the cells and fluid being withdrawn through the side tap outlet 119.

Although the inventive device and method have been described in terms of filtering white blood cells, this description is not to be construed as a limitation on the scope of the invention. It will be apparent to those skilled in the art that various modifications and variations can be made to the structure and methodology of the present invention without departing from the scope or spirit of the invention. Rather, the invention is intended to cover modifications and variations provided they come within the scope of the following claims and their equivalents.

What is claimed is:

1. A blood cell collection system comprising
   a centrifuge rotor;
   a blood processing chamber mounted on said rotor;
   a generally frustro-conical cell separation chamber in fluid communication with said blood processing chamber;
   the cell separation chamber having an inlet and an outlet, said inlet being connected to said blood processing chamber, and
   a side tap outlet on said cell separation chamber, said side tap outlet being adjacent said inlet, and
   means for selectively drawing fluid from either said outlet or said side tap outlet.

2. The blood cell collection system of claim 1 wherein said inlet protrudes into said cell separation chamber.

3. The blood collection system according to claim 2 wherein said protruding inlet has a generally frustro-conical inner surface that slants radially outwardly from said inlet to a mouth of said protruding inlet, said mouth opening into said separation chamber.

4. The blood cell collection system of claim 2 wherein said cell separation chamber further comprises a circumferential well between said protruding inlet and an inner wall of said cell separation chamber and wherein said side tap outlet opens into said well.

5. The blood cell collection system of claim 1 wherein said means for drawing fluid comprise a first line fluidly connected to said outlet and a second line fluidly connected to said side tap outlet.

6. The blood cell collection system of claim 5 wherein each of said first and second lines are fluidly connected to an extracorporeal tubing circuit, said extracorporeal tubing circuit interfacing with a pump assembly.

7. The blood cell collection system of claim 6 wherein said means for selectively drawing fluid from either said outlet or said side tap outlet further comprises a valve that selectively closes or opens said first and second lines.

8. The blood cell collection system of claim 7 wherein said valve is mounted on a stationary portion of said blood cell collection system.

9. The blood cell collection system of claim 7 wherein said first and second lines are fluidly connected together downstream from said valve into a common line.

10. The blood cell collection system of claim 9 wherein said means for selectively drawing fluid further comprises a pump coupled to said common line.

11. The blood cell collection system of claim 10 wherein said means for selectively drawing fluid further comprises a collect tube fluidly connected to said common line for collecting fluid components and a connection line fluidly connected to said common line for returning fluid components to a donor.

12. The blood cell collection system of claim 11 further comprising a valve for selectively permitting flow of said fluid components in said collect tube or said connection line.

13. A disposable blood separation set comprising
   a circumferential blood processing chamber adapted to be mounted on a centrifuge rotor;
   a generally frustro-conical cell separation chamber in fluid communication with said blood processing chamber and adapted to be mounted on said centrifuge rotor;
   the cell separation chamber having an inlet and an outlet, said inlet being connected to said blood processing chamber, and
   a side tap outlet on said cell separation chamber, said side tap outlet being adjacent said inlet, and
   means for selectively drawing fluid from either said outlet or said side tap outlet.

14. The disposable blood separation set of claim 13 wherein said inlet protrudes into said cell separation chamber.

15. The disposable blood separation set according to claim 14 wherein said protruding inlet has a generally frustro-conical inner surface that slants radially outwardly from said inlet to a mouth of said protruding inlet, said mouth opening into said separation chamber.

16. The disposable blood separation set of claim 14 wherein said cell separation chamber further comprises a circumferential well between said protruding inlet and said inner wall and wherein said side tap outlet opens into said well.

17. The disposable blood separation set of claim 13 wherein said means for drawing fluid comprise a first line fluidly connected to said outlet and a second line fluidly connected to said side tap outlet.

18. The disposable blood separation set of claim 17 wherein each of said first and second lines are fluidly connected to an extracorporeal tubing circuit.

19. The disposable blood separation set of claim 17 wherein said first and second lines are fluidly connected together into a common line.

20. The disposable blood separation set of claim 19 wherein said means for selectively drawing fluid further comprises a collect tube fluidly connected to said common line for collecting fluid components and a connection line fluidly connected to said common line for returning fluid components to a donor.

* * * * *